United States Patent [19]

Yafuso et al.

[11] Patent Number: 5,081,041
[45] Date of Patent: Jan. 14, 1992

[54] IONIC COMPONENT SENSOR AND METHOD FOR MAKING AND USING SAME

[75] Inventors: Masao Yafuso, El Toro; Evan A. Thompson, Pasadena; John L. Dektar, Irvine; James F. Fagan, La Jolla; Sanjay L. Patil, Lake Forest, all of Calif.

[73] Assignee: Minnesota Mining and Manufacturing Company, St. Paul, Minn.

[21] Appl. No.: 503,838

[22] Filed: Apr. 3, 1990

[51] Int. Cl.⁵ .................... G01N 21/27; G01N 31/22
[52] U.S. Cl. ........................... 436/68; 356/402; 422/57; 422/58; 422/82.06; 422/82.07; 422/82.08; 427/2; 436/172
[58] Field of Search ............... 422/58, 82.06–82.09, 422/57; 436/68, 172; 128/634; 350/96.3, 96.33; 427/2; 356/39, 402, 410; 385/12

[56] References Cited

U.S. PATENT DOCUMENTS

| Re. 31,879 | 5/1985 | Lubbers et al. | 436/133 |
|---|---|---|---|
| 3,449,080 | 6/1969 | Edwards . | |
| 3,865,548 | 2/1975 | Padawar . | |
| 3,904,373 | 9/1975 | Harper . | |
| 4,194,877 | 3/1980 | Peterson . | |
| 4,321,057 | 3/1982 | Buckles | 422/58 |
| 4,543,335 | 9/1985 | Sommer et al. | 436/69 |
| 4,548,907 | 10/1985 | Seitz et al. | 436/163 |
| 4,557,900 | 12/1985 | Heitzmann | 422/55 |
| 4,568,518 | 2/1986 | Wolfbeis et al. | 422/56 |
| 4,577,109 | 3/1986 | Hirschfeld | 250/461.1 |
| 4,600,310 | 7/1986 | Cramp et al. | 356/432 |
| 4,637,978 | 1/1987 | Dappen | 435/11 |
| 4,640,820 | 2/1987 | Cooper | 436/68 |
| 4,775,514 | 10/1988 | Barnikol et al. | 436/172 X |
| 4,801,551 | 1/1989 | Byers et al. | 436/133 |
| 4,824,789 | 4/1989 | Yafuso et al. | 436/68 |
| 4,833,091 | 5/1989 | Leader et al. | 436/133 |
| 4,851,195 | 7/1989 | Matthews et al. | 422/58 |
| 4,919,891 | 4/1990 | Yafuso et al. | 422/82.08 X |
| 4,954,318 | 9/1990 | Yafuso et al. | 422/82.08 X |

OTHER PUBLICATIONS

Yafuso et al., U.S. patent application Ser. No. 07/496,561, filed 03/20/90.

Zhujun et al, Analytica Chimica Acta, 160 (1984), pp. 305–309.

*Primary Examiner*—Jill Johnston
*Attorney, Agent, or Firm*—Gary L. Griswold; Walter N. Kirn; Dale E. Hulse

[57] ABSTRACT

A composition of matter useful in a sensor for sensing the concentration of an ionic component in a medium is disclosed. This composition comprises a first material which includes a sensing component in an amount effective to provide a signal which varies as the concentration of the ionic component in the medium varies, and a first matrix material which is permeable to the ionic component; and a second material which includes a second matrix material which is permeable to the ionic component, and an opaque agent in an amount sufficient to render the second material effectively opaque. The first material matrix and the second matrix material are covalently bonded together. Sensing apparatus including such composition of matter and methods for making and using such composition of matter are also disclosed.

34 Claims, 1 Drawing Sheet

IONIC COMPONENT SENSOR AND METHOD FOR MAKING AND USING SAME

BACKGROUND OF THE INVENTION

This invention relates to a system for sensing ionic components. More particularly, the invention relates to sensors, and methods for making and using sensors, useful in sensing ionic components, e.g., hydrogen ions or hydroxyl ions-measured by pH, in fluids, such as blood.

It is often advantageous to determine the concentration of an ionic component in a given fluid. For example, medical diagnostic and/or treatment procedures may involve the determination of the pH value of a patient's blood or other bodily fluids. Such determinations may be made very frequently, even continuously, during the procedure.

For biological fluids, a prior known sensor uses the fluorescent properties of a dye in conjunction with the ionic permeability of a preformed integral cellulose membrane sheet. In this sensor, the cellulose membrane is chemically treated so as to introduce covalent bondable groups onto the membrane. A fluorescent dye, suitable for providing a signal which varies as the concentration of the ionic component of interest varies, is then covalently bonded to these groups to adhere the dye to the membrane. A small disc is cut from the membrane sheet and is placed in a well of a sensor cassette, which itself is placed in proximity to an optical fiber. An opaque overcoat is physically placed over the exposed surface of the disc and is secured, e.g., heat staked, to the cassette. This overcoat, which is physically separate from the disc provides optical isolation for the dye in the disc. When the dye is excited by excitation light imposed on the dye, it undergoes fluorescence, emitting a light signal. This emission light signal is transmitted, by the optical fiber, to a processor where it is analyzed to provide a determination of the concentration of the ionic component of interest.

One problem which exists with such membrane-type sensors relates to response time. Such sensors are relatively slow to respond to changes in ionic component concentration. Sensor response time is particularly important in situations where a patient's blood is frequently, or even continuously, monitored and the information obtained from such monitoring is used as a basis for treating the patient. The separate opaque overcoat may contribute to the reduced response time of such sensors, and may cause a variability in the response so that unreliable signals are provided. Further, the separate overcoat has a disadvantageous tendency to be displaced during use, and the heat staking technique can compromise the sterility of the blood flow path.

A faster, more reliable and durable sensor for ionic components, in particular hydrogen ions or hydroxyl ions-measured by pH, would be advantageous.

SUMMARY OF THE INVENTION

A new composition, sensor and methods for making and using the same useful in sensing the concentration of an ionic component in a medium have been discovered. The present compositions provide ionic component sensors, in particular pH sensors, which have rapid response times, provide reliable responses and are physically stable and durable in use. These compositions are structured to have a unitary character while, at the same time providing an acceptable sensing signal and being sufficiently optically isolated. Also, these compositions can be effectively used without compromising the sterility of the fluid flow path. The present method of making ionic component sensors is straightforward and effective, particularly for producing large numbers of ionic component sensors, and produces a highly reliable product. The present system takes advantage of chemically bonding together materials in different parts of the sensor. Such chemical bonding allows one to produce and use a sensor which provides substantial advantages.

In one broad aspect of the present invention, a composition of matter, e.g., sensing composition, useful in sensing the concentration of an ionic component in a medium is provided. This composition comprises a first material, e.g., a first layer, including a sensing component in an amount effective to provide a signal which varies as the concentration of the ionic component of interest in the medium varies, and a first matrix material permeable to the ionic component of interest, and which preferably acts as a carrier for the sensing component. A second material, e.g., a second layer, is provided which includes a second matrix material which is permeable to the ionic component of interest, and an opaque agent in an amount effective to render the second material effectively opaque. The second matrix material preferably acts as, and is present in an amount effective to be, a carrier for the opaque agent. The first matrix material and the second matrix material are covalently bonded together so that there is a substantial bond between the first material and the second material. Thus, the second material, which may be considered an overcoat of the first material, is an integral part of the composition, provides the desired opacity, e.g., for optical isolation of the sensing component in the first material, and yet allows a substantial portion of the sensing component to be substantially free and clear of the opaque agent. Thus, not only is the composition structured to be stable and durable in use, but also the sensing component is able to provide an accurate and reliable signal in response to the concentration of the ionic component of interest in the medium. Importantly, the response time of this sensing composition is very good. That is, the emitted signal from the sensing composition responds rapidly to variations in the concentration of the ionic component of interest in the medium being monitored.

In another broad aspect of the invention, an apparatus useful in sensing the concentration of an ionic component in a medium is provided. This apparatus comprises a sensor means including a quantity of the sensing composition described above. In addition, the apparatus further includes signal means, e.g., one or more optical fibers, capable of transmitting a signal from the sensing component.

The above-noted composition and apparatus can be used in a method for sensing the concentration of an ionic component in a medium. This method comprises contacting the composition or sensor means of the apparatus with the medium to be monitored. The signal given off by the sensing component is analyzed, e.g., using conventional and well known techniques, to determine the concentration of the ionic component of interest in the medium.

In a further broad aspect of the present invention, a method for making a sensor useful in sensing the concentration of an ionic component in a medium is provided. This manufacturing method comprises applying a second composition to a surface of a first composition to form a first composite composition. The first composition comprises a first matrix material precursor, preferably which is solid. The second composition comprises a second matrix material precursor and an opaque agent. This first composite composition is contacted at conditions effective to form a first matrix material and a second matrix material which are covalently bonded together. The first matrix material is contacted with a sensing component or a sensing component precursor at conditions effective to form a sensing composition including an effective amount of the sensing component. The sensor produced in accordance with this method has substantially all the advantages of the sensing composition described previously.

These and other aspects and advantages of the present invention are set forth in the following detailed description and claims, particularly when considered in conjunction with the accompanying drawing in which like parts bear like reference numerals.

DETAILED DESCRIPTION OF THE INVENTION AND DRAWING

Figure 1:
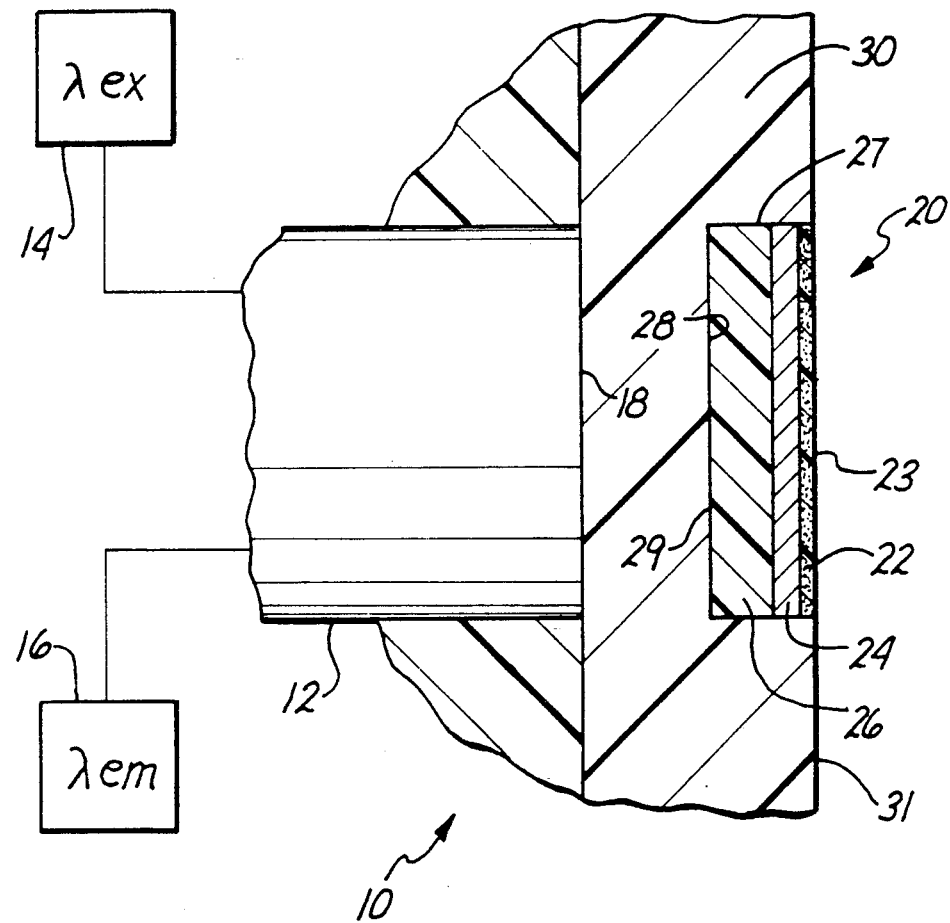
FIG. 1 is a schematic illustration of a sensor apparatus according to the present invention.

The present ionic component sensing compositions include a first material, e.g., a first layer, including a first matrix material and a second material, e.g., a second layer, including a second matrix material. These two matrix materials are covalently bonded together at at least one location in the composition, preferably at or near where the first and second materials physically approach, or even touch, each other. Preferably, the matrix materials are covalently bonded together at or near substantially all the locations where the first and second materials physically approach each other. In one embodiment, the present sensing composition comprises a first zone including all the components of the first material; and a second zone including all the components of the second material. This covalently bonded structure provides a physically stable sensing composition which is durable in use. In addition, and quite importantly, these covalently bonded sensing compositions provide highly reliable sensing signals and are highly responsive to changes in the concentration in the ionic component of interest in the medium being monitored.

The first material of the sensing compositions includes a sensing component in an amount effective to provide a signal which varies in response to variations in the concentration of the ionic component of interest in the monitored medium, and a first matrix material which is permeable to this ionic component of interest. The second material includes a second matrix material, and an opaque agent in an amount effective to render the second material effectively, e.g., for ionic component sensing, opaque.

The signal provided by the sensing component or components in response to the presence of the ionic component in the medium varies as the concentration of the ionic component in the medium being monitored varies. Many sensing components useful to provide a concentration variable signal in response to ionic components are conventional and well known in the art and can be used in the present invention. Examples of the ionic components which can be sensed include hydrogen ions ($H^+$), hydroxyl ions ($OH^-$), metal ions, such as alkali and alkaline earth metal ions, e.g., potassium ions ($K^+$), sodium ions ($Na^+$), lithium ions ($Li^+$) and calcium ions ($Ca^{++}$), and the like.

Any suitable sensing component may be employed in the present invention provided that the sensing component has no substantial detrimental effect on the functioning of the present system or on the medium being monitored. The sensing component is preferably an optical indicator, such as a absorbance indicator or a fluorescence indicator. More preferably, the sensing component is a fluorescence indicator. The present invention is particularly useful in sensing the concentration of hydrogen ions ($H^+$) or hydroxyl ions ($OH^-$). In this embodiment, the pH of the medium is the most often determined. Suitable pH sensing components include many well known pH indicators and/or functionalized derivatives of such indicators. Among the useful pH sensing components are hydroxypyrene 3,6,8- trisulfonic acid (hereinafter referred to as HPTS or hydroxypyrene trisulfonic acid) and derivatives, e.g., salts, thereof, phenolphthalein, fluorescein, phenol red, cresol red, pararosaniline, magenta red, xylenol blue, bromocresol purple, bromphenol blue, bromothymol blue, metacresol purple, thymol blue, bromophenol blue, bromothymol blue, tetrabromophenol blue, bromchlorphenol blue, bromocresol green, chlorphenol red, o-cresolphthalein, thymolphthalein, metanil yellow, diphenylamine, N, N-dimethylaniline, indigo blue, alizarin, alizarin yellow GG, alizarin yellow R, congo red, methyl red, methyl orange, orange I, orange II, nile blue A, ethyl bis (2,4-dinitrophenyl) acetate, gamma-naphthoibenzein, methyl violet 6B, 2, 5-dinitrophenol, and/or the various functionalized derivatives of the above species.

Sensing components for other ionic components can be made from organic species which include fluorescein, diiodofluorescein, dichlorofluorescin, phenosafranin, rose bengal, eosin I bluish, eosin yellowish, magneson, tartrazine, eriochrome black T, coumarin, alizarin and others.

The preferred pH sensing component is hydroxypyrene trisulfonic acid, derivatives of hydroxypyrene trisulfonic acid and mixtures thereof.

The amount of sensing component employed should be sufficient to provide an ionic component concentration dependent signal which is sufficient, e.g., is of sufficient intensity, to be transmitted and analyzed in determining the concentration of the ionic component of interest in the medium being monitored. The specific amount of sensing component employed varies depending, for example, on the specific sensing component being employed, the ionic component being sensed, the medium being monitored, and the other components of the sensor system being employed.

The first and/or second matrix materials useful in the present invention are permeable to the ionic component of interest, and are preferably substantially insoluble in the medium to be monitored. That is, the first and second matrix materials should be structured so that the ionic component of interest can physically permeate such matrix materials. Any suitable first and second matrix materials may be employed provided that such matrix materials have no substantial detrimental effect on the functioning of the system or on the medium being monitored.

Each of the first and second matrix materials is preferably a polymeric material. Macromolecular hydrophilic polymers which are substantially insoluble in the medium to be monitored and permeable to the ionic component of interest are particularly useful as first and/or second matrix materials, e.g., in systems used to monitor aqueous media. Such polymers include, for example, cellulosic materials, high molecular weight or crosslinked polyvinyl alcohol (i.e., PVA), dextran, crosslinked dextran, polyurethanes, quaternarized polystyrenes, sulfonated polystyrenes, polyacrylamides, polyhydroxyalkyl acrylates, polyvinyl pyrrolidones, hydrophilic polyamides, polyesters and mixtures thereof. Preferably the second matrix material is crosslinked. More preferably, both the first and second matrix materials are crosslinked. In a particularly useful embodiment, the first matrix material is cellulosic, especially crosslinked cellulose. With a cellulosic first matrix material, the second matrix material is preferably derived from dextran, and is more preferably crosslinked dextran. Each of the first and second matrix materials, in particular the second matrix material, can be derived from one or more water soluble materials.

The matrix material polymers can be anionic or cationic in character, as desired, and can be made so using conventional and well known techniques. For example, such polymers, or functionalized derivatives thereof, may be reacted with an acidic component, such as an organic sulfonic acid, a carboxylic acid and the like, to form anionic polymers; or may be reacted with a basic component, such as an organic amine and the like, to form cationic polymers.

The sensing component may be bonded, physically or chemically, to the first matrix material. Alternately, the first material may include a physical mixture containing the sensing component and first matrix material. The sensing component is preferably chemically bonded, in particular covalently bonded, to the first matrix material.

The amount of first matrix material used may vary depending, for example, on the specific first matrix material and sensing component being employed. Such first matrix material is preferably present in an amount effective to act as a carrier for the sensing component and/or as a filler to provide additional volume or substance to the first material. Since the first matrix material is permeable to the ionic component of interest, this first matrix material facilitates interaction between this ionic component and the sensing component which results in the ionic component concentration variable signal, described herein. The sensing component is preferably substantially uniformly distributed in the first material.

Any opaque agent may be used provided that such agent or agents function to provide the desired degree of opacity, e.g., for effective optical isolation of the sensing component, and have no substantial detrimental effect on the functioning of the present system or on the medium being monitored. Among the opaque agents useful in the present invention are carbon black, other carbon-based opaque agents, ferric oxide, metallic phthalocyanines and the like. Such opaque agents are preferably substantially uniformly dispersed in the second material in an amount effective to provide the desired degree of opacity, e.g., to provide the desired optical isolation. A particularly useful opaque agent is carbon black.

The amount of second matrix material used may vary depending, for example, on the specific second matrix material and opaque agent being employed. Such second matrix material preferably acts as a carrier or binder to provide additional volume or substance to the second material.

The relative sizes or amounts of the first and second materials may vary widely, provided that the present sensing compositions function as described herein. In order to obtain highly favorable sensor response times, it is preferred that the second material be relatively small compared to the amount of first material. Of course, the second material should have sufficient volume or thickness to provide the sensing composition with the desired opacity, e.g., optical isolation. In a useful embodiment, where the pH of blood is being monitored using a hydroxypyrene trisulfonic acid sensing component, crosslinked cellulose is employed as the first matrix material, crosslinked dextran is employed as the second matrix material and carbon black as the opaque agent, the relative volume or thickness of the first material or first layer to the second material or second layer, respectively, is preferably in the range of about 1 to 0.01 to about 1 to 0.5.

The present sensing compositions may be, and preferably are, prepared using the following method. A quantity, e.g., a sheet, of a first composition is provided. This first composition, which includes a first matrix material precursor, is preferably situated on a flat, e.g., glass, surface in a frame or other fixture, e.g., to facilitate handling and/or processing. This first composition preferably includes a permeability agent which acts to maintain the first matrix material sufficiently porous so that the resulting first matrix material is permeable to the ionic component of interest. The permeability agent preferably has no substantial detrimental effect on the method of making the sensing compositions or on the sensing compositions. For example, if the first matrix material is cellulose, a particularly useful permeability agent is dimethyl sulfoxide or DMSO.

A quantity of a second composition is applied to a surface of the first composition to form a first composite composition. This second composition includes a second matrix material precursor and an opaque agent. Preferably, the second matrix material precursor is solubilized in a liquid medium, e.g., an aqueous-based liquid medium. Thus, the second composition preferably is an aqueous dispersion containing solubilized second matrix material precursor, e.g., water soluble dextran, and fine particles of opaque agent, e.g., carbon black. The second composition may also include an effective amount of a dispersing agent to maintain a substantially uniform dispersion of the opaque agent. In a particularly useful embodiment, the second composition further includes a relatively small amount of a crosslinking agent effective to react with a portion of the crosslinkable sites in the second matrix material precursor to partially crosslink this precursor. A basic material, e.g., sodium hydroxide, may be included in the second composition to promote the crosslinking reaction. The inclusion of this limited amount of crosslinking agent in the second composition facilitates maintaining the second composition on the surface of the first composition and further processing of the first composite composition.

After the second composition is applied to the first composition, and allowed to dry if necessary, the first composite composition is contacted at conditions effective to form the first matrix material and the second matrix material which are covalently bonded together. A particularly useful embodiment involves subjecting the first composite composition to the action of a crosslinking agent so as to form crosslinks between the first and second matrix materials. Preferably, both the first matrix material and the second matrix material include crosslinks in addition to the crosslinks between the first and second matrix materials. Thus, preferably both of the matrix materials are crosslinked and are covalently bonded together, also by crosslinks. This result can be accomplished by contacting the first composite composition with crosslinking agent solution, preferably a basic aqueous crosslinking agent solution. The desired crosslinks are allowed to form resulting in a second composite composition. This second composite composition includes a first matrix material, e.g., crosslinked cellulose, covalently bonded to a second matrix material, e.g., crosslinked dextran, with an opaque agent, e.g., carbon black, dispersed in the second matrix material.

The first matrix material is contacted with a sensing component or a sensing component precursor at conditions effective to form a sensing composition including the sensing component in an amount effective to provide a signal which varies as the concentration of the ionic component in the medium varies. The contacting step may involve repeating this contacting one or more times to provide the desired amount of sensing component in the first material. The sensing component may be physically combined or mixed with the first matrix material. Preferably, however, the sensing component is chemically bonded, more preferably covalently bonded, to the first matrix material.

Chemical bonding of the sensing component to the first matrix material can be accomplished either by direct coupling of the sensing component to reactive sites on the first matrix material, as for instance, the hydroxyl groups on either cellulose or PVA, or through indirect coupling utilizing a substituent group which is coupled or chemically bound to the first matrix material. For example, alkyldiamines can be first joined to at least a portion of the hydroxyl groups on the cellulose backbone by forming a bond between one amino group of the alkyldiamine and the modified cellulose backbone. This leaves one amino functionality of the alkyldiamine available for reaction with the sensing component or sensing component precursor to join the sensing component to the first matrix material.

In one particularly useful embodiment, the above-noted second composite composition is contacted one or more times with a sensing component precursor, e.g., a solution of a sensing component precursor. This precursor is selected so as to form covalent bonds with the first matrix material in the second composite composition. This precursor may also form covalent bonds with the second matrix material in the second composite composition. As a result of this contacting step, sufficient sensing component is covalently bonded to the first matrix material to provide the desired signal.

An individual sensing element can be obtained by removing, e.g., cutting, a properly sized portion of the second composite material including the sensing component from the sheet of such second composite material which has been prepared. The second composite material and/or the individual sensing element or elements can be tested and/or screened, using conventional techniques, to determine its efficacy in measuring the concentration of the ionic component of interest. Such tests, for example, may seek to determine the intensity of the signal provided by the sensing element and/or the response time of the sensing element to changes in the concentration of the ionic component of interest.

If the sensing element is satisfactory, it is then placed at least partially in an open-ended cavity in a sensor holder. Preferably, the sensing element is secured, e.g., by adhesive, to the sensor holder. The sensing element is situated relative to the sensor holder so that the first material is preferably located relatively near to and facing the bottom of the open-ended cavity and the second material is exposed to the medium being monitored.

The sensor holder is preferably placed in proximity to an optical fiber such that signals from the sensing composition can be transmitted by the optical fiber to a processor so that the concentration of the ionic component of interest in the medium can be determined based upon such signals.

The sensing compositions, e.g., in the form of individual sensing elements, of the present invention are useful in a method for sensing the concentration of an ionic component in a medium, preferably a fluid medium, and in particular blood. The medium to be monitored is contacted with the sensing composition. The sensing component in the sensing composition, preferably in the first material of the sensing composition, is caused to emit a signal which varies as the concentration of the ionic component of interest in the medium being monitored varies. For example, when a fluorescence sensing component is used, a light signal of one wavelength is directed toward the sensing component in the sensing composition. This "excitation" signal is designed to cause the sensing component to fluoresce and thereby emit a signal which is dependent on the concentration of the ionic component of interest in the medium being monitored. This "emission" signal is analyzed, e.g., using techniques which are known in the art, to determine the concentration of the ionic component of interest in the medium being monitored.

In a particularly useful embodiment, an optical fiber is used to transmit the "emission" signal from the sensing component. More particularly, the same optical fiber is used to transmit the "excitation" signal to the sensing component and to transmit the "emission" signal from the sensing component.

The following non-limiting example illustrates certain aspects of the present invention.

EXAMPLE

A pH sensor was made as follows. An aqueous dispersion was prepared by combining 300 mg of water soluble dextran, 15 g of deionized water, 300 mg of fine particles of carbon black and 150 mg of a dispersing agent sold by Daishowa Chemicals, Inc. under the trademark Merasperse CBOS4. This dispersion was subjected to ultrasonic mixing four (4) times for a period of two (2) minutes each time, with the dispersion being shaken between periods of ultrasonic mixing. The temperature of the dispersion was maintained below 60° C. throughout the above preparation/mixing procedure.

160 mg of an aqueous solution containing 50% by weight of sodium hydroxide was mixed into the dispersion. 300 mg of ethylene glycol diglycidyl ether was then mixed into the dispersion to provide the bulk overcoat material.

A thin (about 0.0005 inches thick) sheet of cellulose infiltrated with glycerol was washed in water three (3) times for a minimum of 10 minutes each time. This treatment substantially removed the glycerol. The sheet was soaked for 30 minutes, with agitation, in an aqueous solution containing 20% by weight of dimethyl sulfoxide. The sheet was then laid on a 10 cm by 10 cm glass plate and excess liquid was removed by rolling a glass rod over the sheet. A plastic frame was clamped on the sheet covered glass plate, and the sheet was allowed to dry.

2.4 g of the bulk overcoat material was applied evenly to the framed sheet. The coated, framed sheet was spun, using a conventional spin coater, for about six (6) minutes until it appeared dry. After spinning, the coated, framed sheet is allowed to dry for at least one half hour.

A crosslinking solution was prepared as follows. 25 g of ethylene glycol diglycidyl ether and 15 g of a freshly made 0.75 molar sodium hydroxide aqueous solution were combined. 5 g of an aqueous solution containing 28% by weight of hexane diamine was added dropwise with stirring over a 10 minute period at ambient temperature. 5 g of dimethyl sulfoxide was added and the solution was placed in a water bath at 25° C. This crosslinking solution was stirred for an additional 20 minutes.

7 g of the crosslinking solution was poured into the frame and came in contact with the coated, framed sheet. After 45 minutes at ambient temperature, excess liquid was poured off. The treated sheet was washed with running tap water. The treated sheet was rinsed two (2) times in deionized water and immersed for 15 minutes in a solution containing one (1) liter of water and 60 cc of an aqueous solution containing 70% by weight of hexane diamine. The treated sheet was then washed in water, and, if necessary, stored in deionized water at about 4° to 10° C.

The sensing component was included in the treated sheet as follows. The treated sheet was soaked for five (5) minutes in an aqueous solution containing 2.5% by weight of sodium carbonate. The treated sheet was then soaked for three (3) minutes in an aqueous solution containing 23.5% by volume of dimethyl formamide. The treated sheet was then soaked for 2.5 minutes in a dimethyl formamide solution containing 0.02% by weight of acetoxypyrenetrisulfonyl chloride, which solution had been aged for 10 minutes.

After this soaking, the treated sheet was rinsed with water and with an aqueous solution containing 2.5% by weight of sodium carbonate. The treated sheet was then soaked in such an aqueous sodium carbonate solution at 70° C. for 30 minutes. The treated sheet was tested for fluorescent intensity, using conventional procedures.

The treated sheet, having acceptable fluorescent intensity, was dehydrated by soaking in methanol. After this, the treated sheet is soaked for 20 minutes in a fresh acetic anhydride solution containing 5% by weight of pyridine. Certain of the excess amine in the treated sheet was acetylated as a result of this soaking. The treated sheet was rinsed with methanol to remove the acetylated amine. The treated sheet was then soaked for 20 minutes in a tetrahydrofuran solution containing 10% by weight of methanesulfonyl chloride and 10% by weight of pyridine. Additional amine in the treated sheet was sulfonylated as a result of this soaking. The treated sheet was again rinsed in methanol, and then in water to remove the sulfonylated amine. The treated sheet was then placed for 20 minutes in an aqueous solution containing 1% by weight of sodium hydroxide to hydrolyze any acetate and sulfonic esters which may have formed on the crosslinked cellulose of the treated sheet. The treated sheet was washed and then allowed to dry. If the treated sheet is to be stored, before drying, it is placed in an aqueous solution containing 20% by weight of glycerol and stored at about 4° to 10° C.

A transparent cassette was provided which included a cavity or well having one open end. This cassette was made of transparent polycarbonate.

After the treated sheet was dry, a disc was cut from the treated sheet. If desired, a number of such discs can be cut from a single treated sheet and used in the same manner as the disc described herein. This disc was of sufficient size, e.g., diameter, to substantially correspond to the cross-sectional area of the cassette well. Using a transparent polyurethane-based adhesive, this disc was bonded to the well so that the opaque covercoat portion or layer of the disc extended away from the bottom of the well.

FIG. 1 shows a pH sensor of the invention, shown generally at 10. An optical fiber 12 is connected to a light transmitting apparatus 14. The light transmitting apparatus 14 generates the excitation light. The optical fiber 12 is also connected to a light receiving apparatus 16. The light receiving apparatus 16 receives and analyzes the emission light from the HPTS fluorescence sensing component as described in Lubbers et al Reissue Pat. No. 31,879 and Heitzman U.S. Pat. No. 4,557,900. Each of these patents is incorporated by reference in its entirety herein.

The optical surface 18 of the fiber 12 is spaced apart from the sensing disc, shown generally at 20. Sensing disc 20 is produced as described in the example herein. Sensing disc 20 includes an opaque layer 22, and a sensing component layer 24. A transparent polyurethane-based adhesive layer 26 bonds sensing disc 20 to well 28. The thickness ratio of opaque layer 22 to sensing component layer 24 to adhesive layer 26 is about 1 to about 5 to about 100. Sensing disc 20 is located in well 28 of cassette 30 as shown in FIG. 1. Well 28 is open at one end, includes a right circular cylindrical side wall 27 and a circular bottom wall 29. Well 28 has a diameter of 0.15 inches and a depth of 0.010±0.0005 inches. The top surface 23 of opaque layer 22 is substantially flush with the inner surface 31 of cassette 30. Cassette 30 is made of transparent polycarbonate. The sterility of the fluid flow path through cassette 30 is not disturbed by the presence of sensing disc 20 in well 28.

In use, the fluid medium the pH of which is to be monitored, e.g., blood, is allowed to come into contact with sensing disc 20, e.g., by flowing this medium in cassette 30 back and forth across sensing disc 20. Excitation light of an appropriate wave length from the light transmitting apparatus 14 is fed to the optical fiber 12, which transmits it toward sensing disc 20. This excitation light interacts with the HPTS in the sensing component layer 24 causing the HPTS to fluoresce and emit a signal which is dependent on the pH of the medium being monitored. The emission light from the fluorescence is transmitted by optical fiber 12 to light receiving apparatus 16 where it is processed and analyzed to determine the pH of the medium being monitored.

While this invention has been described with respect to various specific examples and embodiments, it is to be understood that the invention is not limited thereto and that it can be variously practiced within the scope of the following claims.

What is claimed is:

1. A composite sensing element useful in sensing the concentration of an ionic component in a medium comprising:

a first layer which includes a first matrix material which is permeable to the ionic component, and a sensing component in an amount effective to provide a signal which varies as the concentration of the ionic component in the medium varies; and a second layer which includes a second matrix material which is permeable to the ionic component, and an opaque agent in an amount sufficient to render said second layer effectively opaque, said first layer and said second layer being covalently bonded together, said composite sensing element being formed from a composite sheet comprising said first and second covalently bonded layers, from which composite sheet a plurality of said composite sensing elements may be formed.

2. The element of claim 1 where both said first matrix material and said second matrix material are polymeric and are crosslinked together.

3. The element of claim 1 wherein said first matrix material and said second matrix material have different chemical compositions.

4. The element of claim 1 wherein said second matrix material is crosslinked.

5. The element of claim 1 wherein both first and second matrix materials are crosslinked and said first matrix material and said second matrix material are formed and covalently bonded together by contacting a precursor composite comprising first and second matrix material precursors at conditions effective to form said first and second matrix materials.

6. The element of claim 1 wherein said first matrix material is cellulosic.

7. The element of claim 6 wherein said second matrix material is derived from dextran.

8. The element of claim 1 wherein the ionic component is $H^+$ or $OH^-$.

9. The element of claim 1 wherein said sensing component is an optical indicator.

10. The element of claim 1 wherein said sensing component is a fluorescence indicator.

11. The element of claim 1 wherein said sensing component is selected from the group consisting of hydroxyprene trisulfonic acid, derivatives of hydroxyprene trisulfonic acid and mixtures thereof.

12. The element of claim 1 wherein said second layer acts to substantially optically isolate a portion of said first layer.

13. The element of claim 1 wherein said opaque agent is carbon black.

14. An apparatus useful in sensing the concentration of an ionic component in a medium comprising:

a composite sensing element comprising a first layer which includes a first matrix material which is permeable to the ionic component and a sensing component in an amount effective to provide a signal which varies as the concentration of the ionic component in the medium varies, and a second layer which includes a second matrix material which is permeable to the ionic component and an opaque agent in an amount sufficient to render said second layer effectively opaque, said first layer and said second layer being covalently bonded together, said composite sensing element being formed from a composite sheet comprising said first and second covalently bonded layers, from which composite sheet a plurality of said composite sensing elements may be formed; and signal means capable of transmitting said signal from said sensing component.

15. The apparatus of claim 14 wherein said sensing component is an optical indicator, said first and second matrix materials are crosslinked together and said signal means comprises an optical fiber.

16. The apparatus of claim 15 wherein said first matrix material and said second matrix material are formed and covalently bonded together by contacting a precursor composite comprising first and second matrix material precursors at conditions effective to form said first and second matrix materials.

17. The apparatus of claim 14 wherein said optical fiber is spaced apart from said first layer.

18. The apparatus of claim 17 which further comprises holder means including a cavity having an open end and being sized and adapted to receive at least a portion of said first layer, said composite sensing element being structured and oriented so that said first layer is located away rom said open end of said cavity.

19. The apparatus of claim 18 wherein said holder means is substantially transparent, and said second layer, together with said holder means, substantially completely surrounds said first layer.

20. The apparatus of claim 14 wherein said sensing component is selected from the group consisting of hydroxyprene trisulfonic acid, derivatives of hydroxypyrene trisulfonic acid and mixtures thereof, said first matrix material is cellulosic, said second matrix material is derived from dextran and said opaque agent is carbon black.

21. A method for sensing the concentration of an ionic component in a medium comprising:

contacting said medium with a composite sensing element which comprises a first layer which includes a first matrix material which is permeable to said ionic component and a sensing component in an amount effective to provide a signal which varies as the concentration of said ionic component in said medium varies, and a second layer which includes a second matrix material which is permeable to said ionic component and an opaque agent in an amount sufficient to render said second layer effectively opaque, said first layer and said second layer being covalently bonded together, said composite sensing element being formed from a composite sheet comprising said first and second covalently bonded layers, from which composite sheet a plurality of said composite sensing elements may be formed; and analyzing said signal to determine the concentration of said ionic component in said medium.

22. The method of claim 21 wherein said medium is blood.

23. The method of claim 21 wherein said ionic component is $H^+$ or $OH^-$.

24. The method of claim 21 wherein both said first matrix material and said second matrix material are polymeric, and said first matrix material and said second matrix material are formed and covalently bonded together by contacting a precursor composite comprising first and second matrix material precursors at conditions effective to form said first and second matrix materials.

25. The method of claim 21 wherein said first matrix material is cellulosic, said second matrix material is derived from dextran and said first and second matrix materials are crosslinked together.

26. The method of claim 21 wherein said sensing component is a fluorescence indicator.

27. The method of claim 21 wherein said sensing component is selected from the group consisting of hydroxypyrene trisulfonic acid, derivatives of hydroxypyrene trisulfonic acid salts and mixtures thereof, and said opaque agent is carbon black.

28. A method for making a composite sensing element useful in sensing the concentration of an ionic component in a medium comprising:

applying to a surface of a first composition of a second composition to form a composite composition, said first composition including a first matrix material precursor and said second composition including a second matrix material precursor and an opaque agent;

contacting said composite composition at conditions effective to form a first matrix material in a first layer and a second matrix material containing said opaque agent in a second layer, which layers are covalently bonded together;

contacting said first matrix material with a sensing component or a sensing component precursor at conditions effective to form a composite sensor sheet including said sensing component in an amount effective to provide a signal which varies as the concentration of the ionic component in the medium varies and;

obtaining a plurality of said composite sensing elements from said composite sensor sheet.

29. The method of claim 28 wherein said first matrix material and said second matrix material are permeable to the ionic component.

30. The method of claim 28 wherein an effective amount of a crosslinking agent is included in said composite composition prior to said composite composition contacting step, and said composite composition contacting step acts to form crosslinks between said first matrix material and said second matrix material.

31. The method of claim 30 wherein said first matrix material includes crosslinks and said second matrix material includes crosslinks in addition to the crosslinks between said first matrix material and said second matrix material.

32. The method of claim 28 wherein said sensing component is covalently bonded to said first matrix material.

33. The method of claim 28 wherein said first matrix material is cellulosic and said second matrix material is derived from dextran.

34. The method of claim 28 wherein said sensing component is selected from the group consisting of hydroxypyrene trisulfonic acid, derivatives of hydroxypyrene trisulfonic acid and mixtures thereof.

* * * * *

UNITED STATES PATENT AND TRADEMARK OFFICE
CERTIFICATE OF CORRECTION

PATENT NO. : 5,081,041

DATED : January 14, 1992

INVENTOR(S) : Yafuso et al.

It is certified that error appears in the above-identified patent and that said Letters Patent is hereby corrected as shown below:

Cover page, under the heading "Inventors", Richard B. Phillips of Mountainview, California should be added as a named inventor.

Col. 11, Line 20, "where" should be --wherein--.

Col. 11, Lines 46-47, "hydroxyprene" should be --hydroxypyrene--.

Col. 11, Lines 47-48, "hydroxyprene" should be --hydroxypyrene--.

Col. 12, Line 23, "rom" should be --from--.

Col. 12, Line 30, "hydroxyprene" should be --hydroxypyrene--.

Col. 13, Line 13, delete the second occurrence of "of".

Signed and Sealed this

Sixth Day of April, 1993

Attest:

STEPHEN G. KUNIN

*Attesting Officer*  *Acting Commissioner of Patents and Trademarks*